United States Patent [19]

Aid

[11] Patent Number: 4,773,991
[45] Date of Patent: Sep. 27, 1988

[54] WATER PURIFICATION SYSTEM FLUID PATH

[75] Inventor: James D. Aid, St. Petersburg, Fla.

[73] Assignee: Baxter Travenol Laboratories, Inc., Deerfield, Ill.

[21] Appl. No.: 145,730

[22] Filed: Jan. 15, 1988

Related U.S. Application Data

[63] Continuation of Ser. No. 027,113, Mar. 13, 1987, abandoned, which is a continuation of Ser. No. 790,807, Oct. 25, 1985, abandoned, which is a continuation of Ser. No. 577,091, Feb. 6, 1984, abandoned, which is a continuation of Ser. No. 447,857, Dec. 8, 1982, abandoned.

[51] Int. Cl.$^4$ .............................. B01D 13/00
[52] U.S. Cl. .............................. 210/96.2; 210/136; 210/137; 210/195.2; 210/196; 210/257.2; 210/321.6
[58] Field of Search ............... 210/136, 137, 195.2, 210/196, 257.2, 266, 295, 321.1–321.5, 433.1, 433.2, 96.2, 181

[56] References Cited

U.S. PATENT DOCUMENTS

| | | | |
|---|---|---|---|
| 3,708,069 | 1/1973 | Clark | 210/181 |
| 4,210,533 | 7/1980 | Astz | 210/136 |
| 4,342,651 | 8/1982 | Ahrens | 210/321.1 |
| 4,402,940 | 9/1983 | Nose et al. | 424/101 |
| 4,498,982 | 2/1985 | Skinner | 210/96.2 |

OTHER PUBLICATIONS

Klein, E. et al, "Evaluation of Hemodialyzers and Dialysis Membranes", Artificial Organs, Feb. 1978, vol. 2, No. 1, pp. 35–41.
Sourirajan, S., *Reverse Osmosis*, Academic Press, New York, 1970, p. 444.
Mattson, R. J. et al, "Improved Water Quality", Chem. Eng. Prog., vol. 65, No. 1, Jan. 1969, pp. 62–68.

*Primary Examiner*—Frank Sever
*Attorney, Agent, or Firm*—Paul C. Flattery; Charles R. Mattenson; Kay Pierce

[57] ABSTRACT

A water purification system includes a water purifying module having an inlet, a first outlet for purified product water and a second outlet for untreated concentrate water. An inlet line is connected to the module inlet, a purified water line is connected to the first outlet, and a drain line is connected to the second outlet. A first return line including a check valve is connected between the purified water line and the inlet line, and a second return line is connected between the drain line and the inlet line. Water to be treated is supplied to the inlet line by a pressure regulator, which provides regulated water pressures in the inlet line, the first and second return lines, and the purified water line.

4 Claims, 1 Drawing Sheet

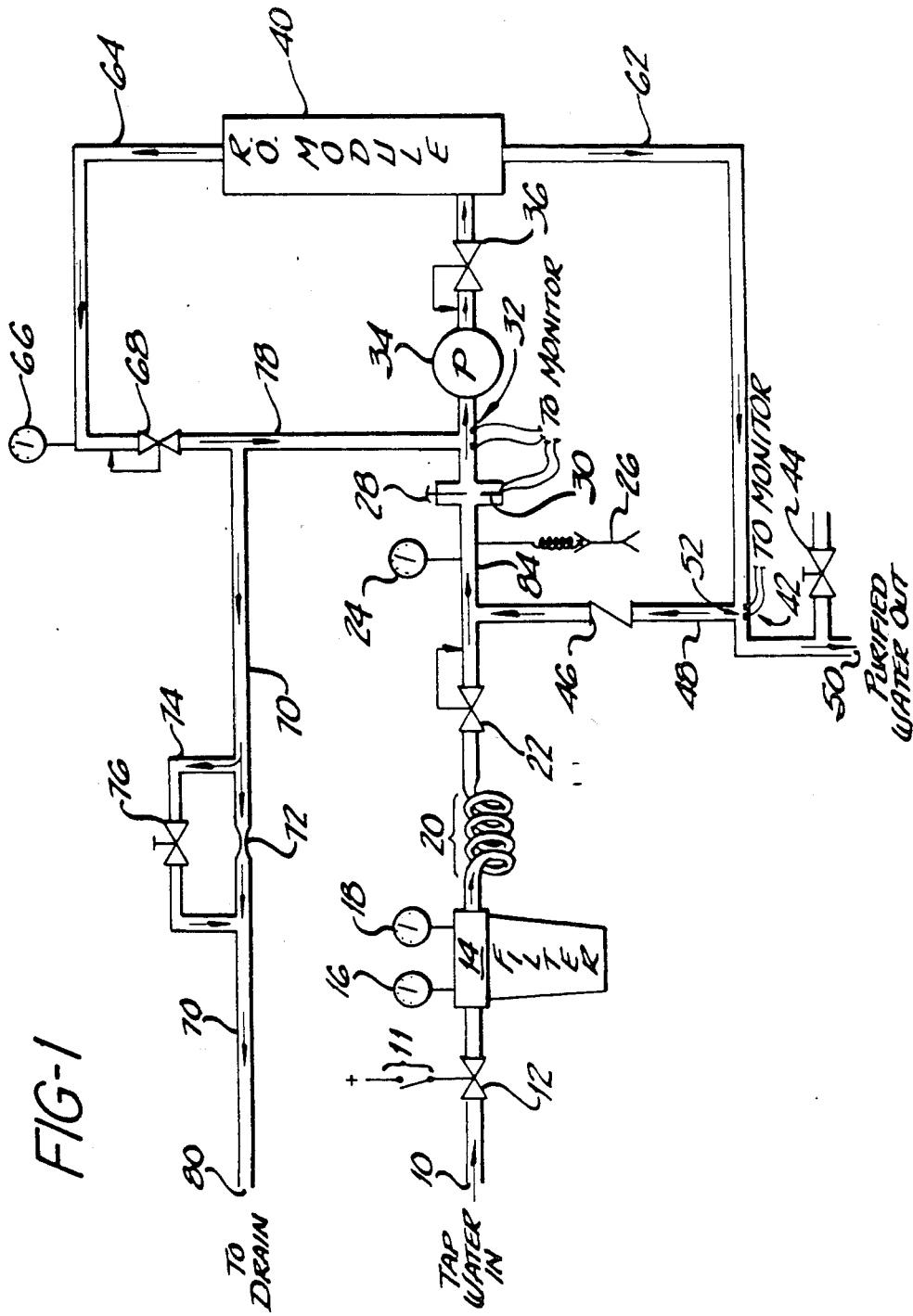

WATER PURIFICATION SYSTEM FLUID PATH

This is a continuation of Ser. No. 07/027,113, filed 03/13/87, which was a continuation of Ser. No. 06/790,807, filed 10/25/85, which was a continuation of Ser. No. 06/577,091, filed 02/06/84, which was a continuation of Ser. No. 06/447,857, filed 12/08/82, all now abandoned.

This invention relates to water purification systems and, in particular, to pressure regulated fluid paths in water purification systems.

The need for purified water frequently arises in a medical setting. For instance, purified water is generally required when performing hemodialysis on a patient requiring such treatment. In hemodialysis, impurities in a patient's blood are removed by diffusing them across a membrane and into a specially prepared dialysate fluid. A considerable amount of dialysate fluid is required for a typical hemodialysis treatment, which fluid is generally prepared using purified water.

One technique used to purify water is the reverse osmosis process. In this process, a stream of untreated water is pumped at elevated pressure into a pressure resistant vessel containing a semipermeable membrane. Some of the water permeates across the membrane and is collected as purified product water in a low pressure output line while the remainder of the original stream exits the vessel, where it is depressurized for recirculation or disposal.

The design of the water paths to and from the reverse osmosis module, which contains the semipermeable membrane, is important in order to efficiently use untreated water, to produce a significant flow of purified product water, and to maintain desired water pressure levels in the system. An advantageous water path arrangement is the dual loop technique, in which both unused product water and untreated concentrate water flowing from the reverse osmosis module are returned to the inlet to the module. High pressure untreated water is applied to the module which produces product water at a first outlet while untreated concentrate water is produced at high pressure at a second outlet. In a dual loop system, unused product water is returned to the module inlet, as is a portion of the untreated concentrate water produced at the second module outlet.

When configuring a dual loop system it is desirable to control water pressures in the various legs of the loops. Untreated water which is applied to the system, generally tap water, must be increased in pressure for the reverse osmosis module. The high pressure untreated concentrate water produced by the module must be lowered in pressure before it can be safely drained from the system. And, it is desirable to regulate the pressure of the purified product water which is provided to a user. Furthermore, it is desirable to provide this pressure regulation in a relatively simple and inexpensive manner which will not contaminate the purified product water.

In accordance with the principles of the present invention, a pressure regulated water path arrangement is provided for a water purification system. A water purification module has an inlet for untreated water, a first outlet at which purified product water is produced, and a second outlet at which untreate concentrate water is produced. The first and second outlets are connected to the inlet water path of the module by first and second water paths, thereby forming a dual loop arrangement. A pressure regulator is located between a source of untreated water and the junctions of the first and second water paths and the inlet water path, and a check valve is located in the first water path. The pressure regulator thereby regulates the water pressure in portions of the inlet, first and second water paths. The check valve provides an inexpensive means of connecting the first water path to the inlet water path, and prevents flow of untreated water into the product water as well as a reduced possibility of contamination of the product water. In addition, the pressure regulator affords an ease in the controlled disposal of brine water from the second module outlet.

In the drawings:

The sole drawing FIG. 1 illustrates schematically the pressure-controlled water path of a reverse osmosis water purification system constructed in accordance with the principles of the present invention.

Referring to FIG. 1, a reverse osmosis system constructed in accordance with the principles of the present invention is shown schematically. Untreated tap water enters the system through an inlet 10, and is passed by an inlet solenoid valve 12 under control of an on/off switch 11. The inlet water enters a filter 14, which filters out particulate matter and removes the chlorine from the inlet water. The filter includes a ten micron carbon impregnated filter element. The chlorine at times must be removed chlorine can damage certain membranes used in the reverse osmosis module. The water pressure at the inlet and outlet of the filter 14 is monitored by gauges 16 and 18. During normal operation the gauge pressure should be virtually the same. A greater than 10 psi differential between the inlet and outlet gauges of the filter 14 indicates that the filter is becoming clogged and should be replaced.

The filtered water then flows through a coil of tubing 20, which is wound around the motor of pump 34 to both cool the motor and warm the water. The inlet water then flows through a pressure regulator 22. The pressure regulator 22 controls the water pressure at its outlet so that the water pressure there will not exceed 20 psi. Depending upon the pressure of the inlet water, water pressure at the input to the pressure regulator can exceed 20 psi. A flow of inlet water, now at approximately 20 psi, enters the inlet line 84 to the pump and reverse osmosis module.

In the inlet line 84, a pressure gauge 24 monitors water pressure to assure the user that water pressure remains at about 20 psi. A one psi check valve 26 is coupled to the inlet line 84 to inject a sanitizing agent such as formalin into the inlet water. The injected formalin is used to sanitize the water since the water now has no chlorine content. The inlet water flows past a pressure switch 28, which turns the system off if water pressure in the inlet line 84 drops below 6 psi. The pressure switch 28 thereby protects the pump against cavitation. A temperature sensor 30 senses the inlet water temperature and provides an output signal to a monitor (not shown). The inlet water also flows past a conductivity cell 32, which also provides an electrical signal for the monitor.

The inlet water then enters the pump 34, which increases the water pressure from about to 20 psi to approximately 200 psi. The pressurized water is applied to the reverse osmosis module 40 by way of a 25 psi check valve 36. This check valve 36 closes when the outlet water pressure of the pump drops below 25 psi to prevent the instantaneous reflection of high water pressure back to the gauge 24 when the pump 34 is turned off. This is to protect the gauge and other components in the low pressure 20 psi loop preceding the pump.

Inlet water, now at 200 psi, enters the reverse osmosis module 40 where some of the water permeates the module membrane to produce purified product water in outlet line 62. The balance of the inlet water which does not permeate the membrane exits the module through a line 64.

The module outlet pressure in line 64 remains at about 200 psi and is monitored by a pressure gauge 66. The reverse osmosis membrane may comprise, for example, a thin-film composite membrane formed by a depositing a thin polymer coating on a microporous polysulfone support layer.

The water pressure in the outlet line 64 is maintained at approximately 200 psi by a back pressure regulator 68, which opens when the water pressure in line 64 exceeds 200 psi. Water passed by the back pressure regulator flows into a drain line 70 and a recirculation line 78. The water in the recirculation line 78 reenters the inlet line 84 at a point opposite the conductivity cell 32. Water in the drain line 70 passes through a 500 cc per minute orifice 72 and then to the drain through an outlet 80. A line 74 bypasses the orifice 72 during rinsing operations, at which time the rinse valve 76 is opened.

Purified product water in line 62 flows past a conductivity cell 42, which detects the level of impurities remaining in the water. The purified water then is free to flow out of an outlet 50. A sampling port 44 may be opened if it is desirable to take a sample of the purified water. When the both the sampling port 44 and the outlet 50 are closed, the purified water pressure builds in a return line 48, which soon opens a one psi check valve 46. The unused purified water then recirculates through the system by reentering the inlet line 84.

In accordance with the principles of the present invention, the pressure regulator 22 maintains the water pressure in the inlet line 84, the recirculation line 78, and the product water lines 62 and 48 at approximately 20 psi. Since the pressure in the inlet line is held at approximately 20 psi, the one psi check valve 46 will open to pass unused product water from line 48 into the inlet line 84 whenever the product water pressure exceeds approximately 21 psi. In the preferred embodiment, the check valve 46 is a spring loaded check valve which prevents any flow of inlet water into the product water lines. Since the product water pressure is controlled by the operation of the check valve in cooperation with the pressure regulator 22, no pressure regulator is necessary for the product water line which affords a considerable cost savings. Moreover, the purity of the product water makes it readily susceptible to contamination from sources such as bacterial growth. The use of a stainless steel check valve for check valve 46 reduces this possibility of contamination as compared to the use of a pressure regulator, since such a check valve does not have all of the ports and surface area of a pressure regulator valve. Thus, the pressure regulator 22, which effectively regulates the product water pressure, is located at a point in the system where water contamination by the pressure regulator is not a concern since pressure regulator 22 is followed by a formalin injection valve 26.

Design and construction of the untreated concentrate water drain portion of the system is made easier by the use of pressure regulator 22, since the water in lines 70 and 78 is thereby maintained at approximately 20 psi. Since the drain orifice 72 is receiving water at a regulated 20 psi pressure instead of the 200 psi exit pressure of the module 40, the orifice 72 can be easily sized for a relatively constant 500 cc per minute flow. The orifice 72 can be sized larger when receiving 20 psi water than 200 psi water for the same desired flow rate. An operational advantage is afforded, since the larger 20 psi orifice will not clog as readily with particulate matter as would a smaller orifice at the same flow rate from a 200 psi source. For even more precise regulation, orifice 72 may comprise a rubber orifice, which is somewhat self-regulating.

The sizing of recirculation line 78 is of importance and should be taken into consideration during system design. Specifically, the water flow rate in recirculation line 78 should be high enough so that the direction of water flow does not reverse during the rinse mode, causing rinse water to flow directly from inlet line 84 to rinse valve 76 by way of lines 78 and 70. This flow reversal may be prevented by sizing recirculation line to a small enough diameter to prevent flow reversal at the desired flow rates and pressures.

It is important to locate conductivity cell 42 at the junction 52 of outlet line 62 and return line 48. When so located, the conductivity cell 42 will measure the conductivity, and hence the impurity, of product water flowing from outlet line 62 into return line 48 and/or through the outlet 50. Furthermore, if check valve 46 should fail and permit untreated water from inlet line 84 to enter lines 48 and 62, conductivity cell 42 is positioned to readily detect this malfunction. If the conductivity cell 42 were to be located further to the right in line 62, untreated water could flow from line 48 to outlet 50 without being detected by the cell. If the conductivity cell 42 were to be located further toward outlet 50, the conductivity cell 42 would be improperly positioned to sense the impurity concentration of the recirculating product water when the outlet 50 is closed, since water beyond junction 52 would be stagnant at this time. This is important when the purification process is advancing from the production of relatively impure water to the production of pure water, as the location of the conductivity cell 42 to the left of junction 52 would prevent the conductivity cell from detecting the improvement in water purity.

What is claimed is:

1. A water purification system comprising:
   a water purification module containing a water purifying membrane, and having an inlet for receiving water to be purified, a first outlet at which purified product water is produced, and a second outlet at which relatively untreated water is produced;
   an inlet water line connected at one end to a source of water and at another end to said module inlet for supplying water to be purified;
   a purified water line having an inlet connected to said first outlet of said module;
   an untreated water drain line having an inlet connected to said second outlet of said module and an outlet for discharging the untreated water;
   a first return line having an inlet connected to said untreated water drain line and an outlet forming a junction with said inlet water line;
   a second return line having an inlet connected to said purified product water line and an outlet forming a junction with said inlet water line;

means for regulating pressure in said purified product water line while preventing introduction of untreated water therein, including, check valve means in said second return line, being located between the inlet of said second return line and the junction of said second return line and said inlet water line, said check valve means thereby forming in said second return line an upstream portion located between the inlet of said second return line and said check valve means and a downstream portion located between said check valve means and the junction of said second return line and said inlet water line, said check valve means being operative for preventing fluid flow in said downstream portion through said check valve means and into said upstream portion, for preventing fluid flow in said upstream portion through said check valve means into said downstream portion when the water pressure in said downstream portion is equal to or greater than the water presure in said upstream portion, and for permitting fluid flow from said upstream portion through said check valve means into said downstream portion when the water presure in said downstream portion is less than the water pressure in said upstream portion; and pressure regulator means in said inlet water line located between the source of water to be purified and the junctions of said first and second return lines with said inlet water line for maintaining the water pressure in said inlet water line, said first return line, and said downstream portion of said second return line at a preselected pressure.

2. The water purification system of claim 1, further comprising:

flow control orifice means located in said untreated water drain line between the junction of said first return line with said drain line and said outlet of said drain line for metering the discharge of water through said drain line outlet in response to the pressure maintained in said first return line by said presure regulator means.

3. The water purification system of claims 1 or 2, and further comprising a conductivity cell for sensing the purity of the purified product water located at said inlet of said second return line.

4. The water purification system of claim 1, wherein said check valve means comprises a one psi check valve.

* * * * *